United States Patent [19]
Palou

[11] Patent Number: 5,350,774
[45] Date of Patent: Sep. 27, 1994

[54] THERAPEUTIC PREPARATION FOR TOPICAL APPLICATION TO THE SKIN

[76] Inventor: Cathy Palou, 342A Marrickville Rd., Marrickville, Australia, NSW 2204

[21] Appl. No.: 905,311

[22] Filed: Jun. 29, 1992

[51] Int. Cl.⁵ .......................... A61K 7/48; A61K 9/06
[52] U.S. Cl. .................................. 514/783; 424/195.1; 514/827; 514/828; 514/859; 514/882; 514/887; 514/944
[58] Field of Search ............... 514/844, 859, 882, 944, 514/828, 827, 887, 183; 424/195.1

[56] References Cited
PUBLICATIONS

The Essential Oils, Jul. 1932, pp. 490 to 492, Finnemore.
The Extra Pharmacopoeia, 1942, 22nd edition, vol. I, pp. 236, 564 and 565, 237.
Pharamaceutical Formulas, 1953, vol. I, 12th edition, pp. 18, 36, 37, 111–115, 377, 536–538, 835–852.

*Primary Examiner*—Dale R. Ore

[57] ABSTRACT

A therapeutic preparation for topical application to the skin for treating skin disorders such as minor burns, abrasions and the like, which contains myrrh oil.

4 Claims, No Drawings

THERAPEUTIC PREPARATION FOR TOPICAL APPLICATION TO THE SKIN

This invention relates to therapeutic preparations, and, in particular, to preparations for topical application to the skin for the treatment of skin disorders.

Cosmetic cream, gel, paste and lotion preparations for topical application for treating skin disorders such as minor burns, cuts, abrasions, coldsores, bedsores or the like are known. The therapeutic properties of herbs are appreciated by some members of the community, and are at times used in the treatment of human-ailments and disorders. For example, the herb Hamamelis, also known as witch-hazel, has been used as a topical astringent and, in the treatment of animals, as an astringent and haemostatic.

The herb Chamomille, with strongly scented foliage and flowers, is best known for its infusion known as Chamomille tea, and has been used as an ingestive relaxant as well as an ingestive remedy for minor stomach disorders and for colds.

Myrrh is a herb sometimes used in incense, and has been administered in the ingestive treatment of humans as a carminative.

The present invention is based on the discovery that the addition of myrrh, even in small amounts, to therapeutic preparations for topical application for the treatment of skin disorders greatly reduces the time necessary for the preparation to have a beneficial effect.

Therefore, according to one aspect, the present invention provides a therapeutic preparation for topical application to the skin for the treatment of skin disorders which contains myrrh and a pharmaceutically suitable non-alcoholic carrier.

According to another aspect, the present invention provides a therapeutic preparation for topical application to the skin for the treatment of skin disorders which contains myrrh, hamamelis, and a pharmaceutically suitable carrier.

According to another aspect the present invention provides a therapeutic preparation for topical application to the skin for the treatment of skin disorders which contains myrrh, hamamelis, chamomille, and a pharmaceutically suitable carrier.

Conveniently, chamomille may take the form of chamomille oil, and hamamelis may take the form of a powder or distilled liquid extract.

For preference, the carrier comprises beeswax.

Such preparations may also include almond oil, olive oil and/or glycerine.

The preparations may also include color, texture or fragrance enhancers, or other herbs.

By way of example three preferred embodiments of the invention will now be described.

Embodiment No. 1

This therapeutic cream preparation contains myrrh, chamomille, hamamelis, almond oil and olive oil in a pharmaceutically suitable carrier, in the following proportions per 580 gm of preparation:

| | |
|---|---|
| Myrrh | 5 milligrams |
| Chamomille | 30 milligrams |
| Almond oil | 100 grams |
| Hamamelis (Extract) | 30 grams |
| Olive oil | 300 grams |

The pharmaceutically suitable carrier for the preparation is beeswax (natural beeswax, for preference).

Further, glycerine is mixed with the above preparation to produce a cream suited for use on bedsores. Glycerine constitutes 20% by weight of the above preparation.

Embodiment No. 2

This therapeutic preparation contains, inter alia, per gram of preparation:

| | |
|---|---|
| Hamamelis extract | 43 mg |
| Chamomille oil | 0.04 mg |
| Myrrh oil | 0.007 mg | as well as glycerine BP and beeswax (natural beeswax, for preference).

This preparation is also suited for use on bedsores.

Embodiment No. 3

This therapeutic cream preparation contains, inter alia, per gram of composition:

| | |
|---|---|
| Hamamelis extract | 52 mg |
| Chamomille oil | 0.05 mg |
| Myrrh oil | 0.009 mg | as well as beeswax (natural beeswax, for preference).

This preparation is suited for use on coldsores, acne, and piles.

The preparations of the preferred embodiments above are all suited for use on minor burns, cuts and abrasions.

The preferred method of using the therapeutic preparation is to apply the cream to the affected area twice daily, after washing the area with warm water and mild soap and drying it thoroughly.

Other modifications and embodiments are possible without departing from the spirit of the invention.

I claim:

1. A substantially alcohol free topical composition for topical application to the skin for the treatment of broken skin disorders comprising an effective amount of myrrh, hamamelis and chamomile in a pharmaceutically acceptable carrier selected from the group consisting of beeswax, glycerine, cream, gel, paste, and lotion.

2. A substantially alcohol free topical composition for topical application to the skin for the treatment of broken skin disorders wherein the broken skin disorders are minor burns, cuts, abrasions, cold sores, bed sores, piles, and ache comprising a pharmaceutically acceptable carrier selected from the group consisting of beeswax, glycerine, cream, gel, paste, and lotion which contains per gram of composition:

52 mg. Hamamelis extract
0.05 mg. Chamomile oil
0.009 mg. Myrrh oil.

3. The topical composition according to claim 1 wherein said composition further comprises an effective amount of at least one of almond oil and olive oil.

4. The topical composition according to claim 1 wherein said composition further comprises an effective amount of at least one of almond oil and olive oil and said pharmaceutically acceptable carrier is at least one of beeswax and glycerine.

* * * * *